United States Patent
Ruffini et al.

(10) Patent No.: US 8,660,649 B2
(45) Date of Patent: Feb. 25, 2014

(54) MULTI-SITE CRANIAL STIMULATION METHOD AND SYSTEM

(75) Inventors: Giulio Ruffini, Barcelona (ES); Esteve Farres, Barcelona (ES); Carles Grau, Barcelona (ES)

(73) Assignee: Starlab Barcelona S.L., Barcelona (ES)

( * ) Notice: Subject to any disclaimer, the term of this patent is extended or adjusted under 35 U.S.C. 154(b) by 178 days.

(21) Appl. No.: 13/058,886

(22) PCT Filed: Oct. 13, 2009

(86) PCT No.: PCT/ES2009/000427
§ 371 (c)(1), (2), (4) Date: Apr. 25, 2011

(87) PCT Pub. No.: WO2010/018275
PCT Pub. Date: Feb. 18, 2010

(65) Prior Publication Data
US 2011/0190846 A1    Aug. 4, 2011

(30) Foreign Application Priority Data
Aug. 13, 2008  (ES) .................................. 200802423

(51) Int. Cl.
*A61N 1/00*  (2006.01)
*A61B 5/04*  (2006.01)
(52) U.S. Cl.
USPC .................. 607/45; 607/2; 607/117; 600/378
(58) Field of Classification Search
USPC ................. 607/2, 45, 117; 600/378
See application file for complete search history.

(56) References Cited

U.S. PATENT DOCUMENTS

| | | |
|---|---|---|
| 6,488,617 B1 | 12/2002 | Katz |
| 7,257,439 B2 | 8/2007 | Llinas |
| 2004/0138578 A1 | 7/2004 | Pineda |

(Continued)

FOREIGN PATENT DOCUMENTS

| | | |
|---|---|---|
| ES | 2289948 | 2/2008 |
| ES | 1067908 | 7/2008 |

(Continued)

OTHER PUBLICATIONS

T.D. Frank et al., Towards a comprehensive theory of brain activity: Coupled oscillator systems under external forces, Physica D, vol. 144, p. 62-86.*

(Continued)

*Primary Examiner* — Nicole F Lavert
(74) *Attorney, Agent, or Firm* — RatnerPrestia

(57) ABSTRACT

The method includes applying individual stimuli to different regions of a brain the application of specific stimulus signals to corresponding stimulation elements arranged adjacent to the regions of the brain. The method includes constructing one or more simplified models of the brain, or of one or more sectors of the brain, considering the brain or the sector thereof, as appropriate, as a non-linear coupled oscillating system, and includes determining the stimulus signals so that the latter are suitable for exciting one or more natural vibration modes of the non-linear coupled oscillating system. The system includes stimulation elements (E1, E2 . . . En) arranged adjacent to regions of a brain, and an electronic system in connection with the stimulation elements (E1, E2 . . . En) and intended for applying thereto corresponding stimulus signals and for determining same by applying the proposed method.

16 Claims, 1 Drawing Sheet

(56) References Cited

U.S. PATENT DOCUMENTS

| | | |
|---|---|---|
| 2005/0124848 A1 | 6/2005 | Holzner |
| 2006/0161219 A1 | 7/2006 | Mock |
| 2007/0032834 A1 | 2/2007 | Gliner |
| 2007/0179557 A1* | 8/2007 | Maschino et al. ............... 607/45 |
| 2008/0154331 A1 | 6/2008 | John |
| 2009/0024017 A1 | 1/2009 | Ruffini |

FOREIGN PATENT DOCUMENTS

| | | |
|---|---|---|
| WO | 03085546 | 10/2003 |
| WO | 2005065768 | 7/2005 |
| WO | 2007097872 | 8/2007 |
| WO | 2007100427 | 9/2007 |

OTHER PUBLICATIONS

Bar-Yam, Y. et al., "Response of complex networks to stimuli," PNAS, Mar. 30, 2004, 101(3):4341-4345.

Buzsaki, G. et al., "Neuronal Oscillations in Cortical Networks," Science, Jun. 25, 2004, 304:1926-1929.

Cumin, D. et al., "Generalising the Kuramoto model for the study of neuronal synchronisation in the brain," Physica D, 2007, 226:181-196.

Engel, A. et al., "Dynamic Predictions: Oscillations and Synchrony in Top-Down Processing," Nature Reviews Neuroscience, Oct. 2001, 2:704-716.

Frank, T.D. et al., "Towards a comprehensive theory of brain activity: Coupled oscillator systems under external forces," Physica D, 2000, 144:62-86.

Herzog, A. et al., "Structural adaptation in young neocortical networks modeled by spatially coupled oscillators," Proceedings of International Joint Conference on Neural Networks, Aug. 2007, IEEE, pp. 3045-3048.

Ray, C. et al., "Complex networks in brain electrical activity," Europhysics Letters, EPL, 2007, 79:38004.

Varela, F. et al., "The Brainweb: Phase Synchronization and Large-Scale Integration," Nature Reviews Neuroscience, Apr. 2001, 2:229-239.

Wagner, T. et al., "Noninvasive Human Brain Stimulation," Ann. Rev. Biomed. Eng. Apr. 12, 2007, 9:19.1-19.39.

International Search Report of PCT/ES2009/000427 filed Oct. 13, 2009, mailed Jan. 20, 2010.

\* cited by examiner

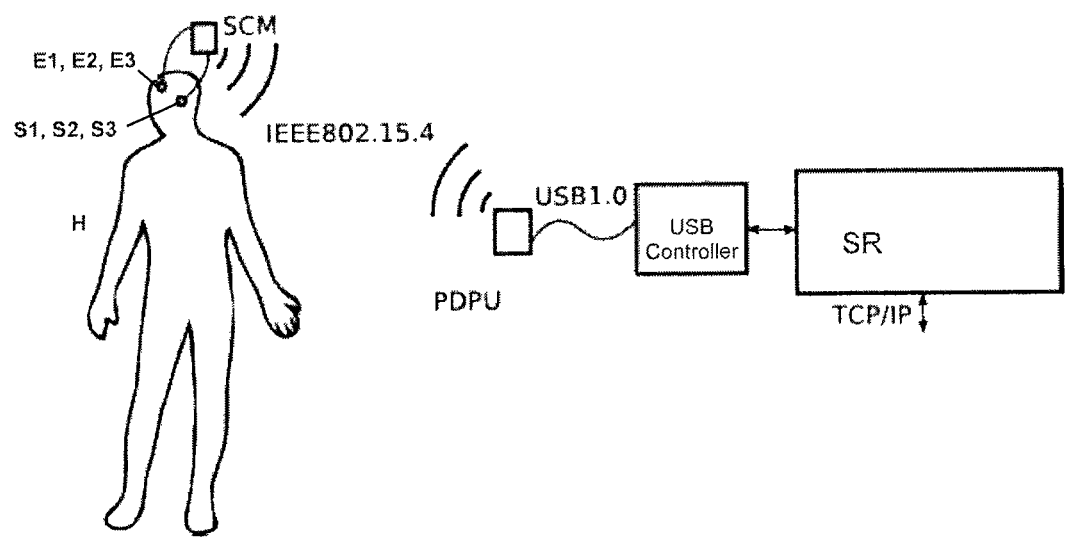

MULTI-SITE CRANIAL STIMULATION METHOD AND SYSTEM

This application is a U.S. National Phase Application of PCT International Application No. PCT/ES2009/000427, filed Oct. 13, 2009.

FIELD OF THE ART

The present invention generally relates to a multi-site cranial stimulation method which comprises applying individual stimuli to different regions of a brain, and particularly to a method which comprises determining the stimulus signals to be applied so that they are suitable for exciting one or more natural vibration modes of the brain, or of a sector thereof seen as a non-linear coupled oscillating system.

The invention also relates to a multi-site cranial stimulation system suitable for implementing the method proposed by the first aspect.

PRIOR ART

Various proposals focusing on both intracranial and transcranial type cranial stimulation either by means of the application of magnetic impulses in the proximity of the regions to be stimulated, or TMS stimulation, or by means of the application of electric signals, including tDCS, ENS or TES stimulation, are known. Some of them use the "multi-site" concept, i.e., the arrangement of a plurality of stimulation elements (electrodes or magnetic coils, depending on if the stimulation is electric or magnetic) in different neural regions to supply a plurality of stimuli. Others also incorporate the feedback concept, i.e., monitoring brain activity to control the stimuli to be applied depending on the monitored signals.

Several of said proposals considered to be representative of the state of the art with respect to cranial stimulation either by magnetic type stimulation or by directly applying electric signals are indicated below.

U.S. Patent Application Publication 2006/0161219 discloses a system and a method for stimulating the nerve tissue in a person's brain by means of the application of electrical pulses in multiple locations for the purpose of treating multiple conditions. Said document indicates that the electrodes by means of which the mentioned stimuli are applied are implanted inside the person's skull. The application proposes applying magnetic stimuli by means of TMS prior to the implantation of the electrodes in order to determine whether the patient is a good candidate for said implantation. The purpose of applying electrodes in multiple locations is to treat several conditions at once, each of them by means of the application of a corresponding stimulation program. U.S. Patent Application Publication 2006/0161219 neither teaches nor suggests treating a single condition by means of the application of stimuli in the mentioned multiple locations to produce a combined effect.

U.S. Pat. No. 7,257,439 proposes a system and a method based on placing a plurality of independent nano-electrodes or ordered assemblies or arrays of nano-electrodes in a blood vessel proximate to a neural tissue, for example brain tissue, for the purpose of monitoring neural activity with some of the electrodes, applying electrical stimuli through other electrodes, and monitoring neural activity again and comparing it to the earlier monitored activity. The main applications proposed include developing a brain-machine interface or enabling artificial limb control.

A series of algorithm for classifying the monitored signals coming from multiple neurons in respective functional states according to spatiotemporal patterns are proposed. No strategies, algorithms or specific programs to carry out neural stimulation are proposed in U.S. Pat. No. 7,257,439. It simply indicates that the monitored signals are analyzed in one way or another depending on the algorithm used, and therefore some decisions or others are made.

In addition, patent document EP1703940A1 (corresponding to WO 2005/065768) proposes a system and a method for administering electrical stimulation (ENS) and magnetic stimulation (TMS) to different regions of the patient's body together or by selecting one of either types of stimulation. It proposes adapting the stimulation parameters depending on the response to the stimulation monitored for example by means of an electroencephalogram (EEG). Examples of parameters to be varied in the case of TMS stimulation are: pulse width, frequency, intensity and orientation of the magnetic field.

U.S. Patent Application Publication 2004/0138578 proposes a system and method for stimulating the brain of a patient depending on bioelectric signals thereof, such as those representative of an EEG. The application describes the real-time adaptation of a TMS stimulation applied to several brain regions by means of using a bidirectional feedback of said bioelectric signals in order to, depending on same, vary the parameters of said stimulation, such as the duration, the time and the pulsating nature of the TMS coils. In its initial phase, the stimulation is also applied depending on a prior monitoring of said bioelectric signals which determine a cognitive-emotive profile of the patient. Said document neither teaches nor suggests performing said stimulation, neither at the beginning nor during the application, depending on variables or premises other than those referring to the mentioned cognitive-emotive profile of the patient.

U.S. Pat. No. 6,488,617 proposes performing a closed loop feedback between, for example, the output of an EEG monitoring system and the control input of a TMS system in order to alter a brain state until reaching the desired state. It proposes controlling different parameters of TMS stimulation (magnitude, movement, duration, etc.). It also indicates the possibility of performing an independent control of the magnets or coils so that each of them generates a single magnetic field at a single frequency. U.S. Pat. No. 6,488,617 neither teaches nor suggests the application of said control to achieve a stimulation where each of the individual stimuli collaborates with the others to achieve a combined effect based on which the characteristics of each of the individual stimuli are previously determined.

One of the most important conclusions reached when analyzing the state of the art is that both TMS and tDCS stimulation lack specificity and suffer from limited focus (Wagner et al, Noninvasive Human Brain Stimulation, Ann. Rev. Biomed. Eng. 2007, 9:19.1-19.39).

Recent studies show that the structural support of brain activity involves the orchestrated activity of different and spatially separated brain regions (see Ray C, Ruffini G, Marco-Pallarés J, Fuintemilla L I, Grau C., Complex networks in brain electrical activity, Europhysics letters. 2007), even with specific frequencies and phases. A truly important challenge in neuroscience is mapping and analyzing spatiotemporal patterns of the activity of large populations of neurons which are believed to be responsible for processing information in the human brain. The brain, with hundred of billions of highly interconnected neurons with information processing based on different times and spatial scales, is perhaps the most interesting system of all complex systems (Buzsaki G, Draguhn A (2004) Neuronal oscillations in cortical networks. Science 304:1926-1929).

The brain can be studied as a pattern modeled tool where the environmental inputs are analyzed once transformed by translation by means of body sensors. The capacity of modeling environmental inputs is crucial for the survival of higher organisms. Neural networks responsible for this task determine if the input information needs to profoundly alter brain dynamics (robustness) or adjust them (response), even dramatically, in order to respond effectively (Bar-Yam and Epstein 2004).

As an example, earlier findings support the idea that the supratemporal and inferior frontal regions work together in data processing to determine the differences between sounds. In this framework, it is considered that a set of spatially distributed group of neurons that are activated in a coherent fashion and form part of the same representation form an association (Engel A K, Fries P, Singer W (2001) Dynamic predictions: Oscillations and synchrony in top-down processing. Nature Reviews Neuroscience 2:704-716). In other words, the brain could be described as a series of local distributed networks of neurons transiently linked by means of dynamic reciprocal connections which support functional integration (Varela F, Lachaux J P, Rodriguez E, Martinerie J (2001) The brainweb: Phase synchronization and large-scale integration. Nature Reviews Neuroscience 2:229-239).

At the same time, it is currently believed that the brain can be better perceived as a non-linear coupled oscillating system in which different areas contribute at the same time in different processes.

Proposals related to multi-site cranial stimulation which takes into account the mentioned approach to the brain as a non-linear coupled oscillating system to determine the individual stimuli to be applied are not known.

DISCLOSURE OF THE INVENTION

It appears to be necessary to provide an alternative to the state of the art which offers a more advantageous cranial stimulation than those known by means of using determination strategies for determining the stimulus signals to be applied which, unlike conventional proposals, take into consideration the mentioned approach to the brain as a non-linear coupled oscillating system in order to better stimulate the entire brain using concepts related to resonance.

To that end the present invention relates in a first aspect to a multi-site cranial stimulation method which comprises applying individual stimuli to different regions of a brain by means of the application of specific stimulus signals to corresponding stimulation elements arranged adjacent to said regions of said brain.

Unlike conventional cranial stimulation proposals, the method proposed by the first aspect of the present invention comprises constructing at least one simplified model of the brain or of a sector thereof, considering the brain or said sector thereof as a non-linear coupled oscillating system, and it comprises determining said stimulus signals so that they are suitable for exciting at least one natural vibration mode of said non-linear coupled oscillating system.

The method comprises performing said application of said stimulus signals in a manner coordinated in space and time, and for one embodiment, it comprises applying part or all of said stimulus signals simultaneously to produce the excitation of one or more natural vibration modes of the brain or of said section thereof by means of the application of said stimulus signals.

As for the regions to be stimulated, these depend on the intervention to be applied, extending substantially throughout the cerebral cortex of the brain for one embodiment.

The method proposed by the first aspect of the present invention comprises monitoring the brain activity of said brain prior to and/or during and/or after the application of said stimulus signals, for example by means of using electrophysiological sensors arranged adjacent to specific regions of the brain.

The mentioned monitoring is carried out by means of the application of any technique known by a person skilled in the art, such as electroencephalography or magnetoencephalography.

One of the purposes of the mentioned monitoring is to provide one or more signals obtained as a result of the monitoring, or monitored signals, to control said stimulation by means of varying said stimulus signals depending on the monitored signals, applying the proposed method. In this manner, the stimulation is adapted or self-calibrated in real time to the changes observed in the brain activity, which is truly advantageous for preventing, up to a certain point, the possible problems and inaccuracies associated with the less reliable positioning of the stimulation elements or with the unknown geometry of the patient's or user's head which, as will be explained below, negatively affect the final distribution of the electric (or magnetic) field on the brain.

In order to carry out the mentioned variation of the stimulus signals, the method comprises independently controlling the phase, frequency and amplitude of each of said stimulus signals to consequently vary the phase, frequency, and amplitude of the induced electric signals.

As for the type of multi-site cranial stimulation to be applied, for one embodiment it is a transcranial magnetic stimulation, said stimulation elements being magnetic coils or emitters suitable for generating magnetic fields depending on the electric signal stimulus applied to them For another embodiment, the multi-site cranial stimulation is an electrical stimulation, said stimulation elements being the corresponding electrodes, and said electrical stimulation, contrary to the conventional direct current stimulation, or tDCS, being a generalized current stimulation, or TCS, i.e., it is not limited to the use of direct current or alternating current, signals with frequencies ranging from 0 Hz up to the maximum desired value, for example 200 Hz, being able to be used.

For one embodiment, the method proposed by the first aspect of the present invention comprises determining the stimulus signals so that they are suitable for exciting several natural vibration modes of said non-linear coupled oscillating system simultaneously or spaced in time either directly and externally, i.e., by means of the express determination of the stimulus signals so that they directly excite each of said natural vibration modes, or naturally in part, in which case the stimulus signals are determined to excite a first natural vibration mode and the rest are excited by means of self-excitation by harmonics or sub-harmonics of the specific stimulus signals to excite the first natural vibration mode.

For one embodiment, the proposed method comprises constructing a plurality of said simplified models for a corresponding plurality of sections of the brain, and it comprises determining and controlling said stimulus signals so that they are suitable for selectively exciting one or more natural vibration modes of one or more of the non-linear coupled oscillating systems corresponding to said simplified models of said sections of the brain.

In other words, the method proposed by the first aspect of the present invention is applicable for stimulating the entire brain or different sections thereof, depending on the envisaged intervention or application, both the complete brain and the different sections thereof being understood in any case as non-linear coupled oscillating systems with specific resonance frequencies, and which are taken into consideration for the determination of the stimulus signals to be applied.

For one embodiment of the proposed method, the mentioned multi-site cranial stimulation is an intracranial stimulation, said stimulation elements used being of the invasive type.

For a preferred embodiment, the multi-site cranial stimulation is a transcranial stimulation, the stimulation elements used being non invasive which, although the proposed method is not limited to the use of one specific type of stimulation elements, for a preferred embodiment, consist of the electrophysiological sensor based on nanostructure conductors proposed in patent application ES2289948, belonging to the present applicant, for the mentioned monitoring, or similar elements for applying stimulus signals for the case in which the stimulation is electrical.

For one embodiment, the proposed method comprises carrying out multi-site transcranial monitoring and stimulation by an electric current, which will be known herein as MtCS, with a fine control of the current flows in the brain, for which the method comprises using at the same time one or more ordered assemblies or arrays of electrodes with a fine and independent control of the phases, amplitudes and frequencies of the stimulus signals to be applied through them in order to provide a space-time modulation of the current flows in different parts of the brain.

For another embodiment, the method comprises controlling several sub-groups of electrodes with a common control signal for each sub-group.

It has been demonstrated in previous studies on electrical stimulation of the brain (in this case tDCS) that the high resistivity of the cranium attenuates the currents which reach the cortex, mostly being steered along the scalp, that both the geometry of the head and the electromagnetic properties of the tissue and the positioning of the electrode all play an important role in determining the final electric field distribution. Such sensitivity requires designing and using a supporting calibration sub-system for the stimulation system in addition to carefully constructing the mentioned simplified model of the brain.

The method proposed by the first aspect of the invention takes into account the mentioned requirements and in order to comply with them, it comprises guiding and calibrating steps responsible for implementing the functions of the mentioned calibration sub-system, and they are carried out as a result of monitoring of the brain activity explained above.

In order to focus the individual stimuli, the proposed method comprises carrying out a first step, or a guiding step, in which the stimulus signals to be applied to the stimulation elements are determined and controlled depending on the brain area (three-dimensional) with respect to which they are adjacently arranged.

To further improved the mentioned focus, the method comprises performing a second step, or calibrating or adjusting step, in which said variation of the stimulus signals is carried out depending on the monitored signals, i.e., depending on the measurements of "what" is causing the (electrical or magnetic) stimulation that is being carried out in order to better adjust it.

The mentioned monitoring signals acquired can include unwanted signals induced by the stimuli, either the stimulus signals directly or signals derived from the application thereof. It is necessary to perform a proper filtering of the monitored signals in order to "clean" said unwanted signals or noise from those which are really indicative of brain activity, be it natural activity or the result of the applied stimulus.

To that end the method proposed by the first aspect of the invention comprises using one or more analysis techniques applied to said monitored signals, obtained for example by means of an EEG, to distinguish between the electric signals induced by the stimuli and natural bioelectric signals or response signals to said stimuli.

For one embodiment, the method comprises using one or more of the following analysis techniques: frequency separation technique, time separation technique and tomography technique, or a combination thereof.

For one embodiment, the proposed method also comprises using spread spectrum techniques applied to said monitored signals to identify the activity associated with the stimulation in each stimulation element.

The method comprises associating a marking signal to each of the stimulus signals, for example by means of superpositioning the same on the corresponding stimulus signal in each stimulation element, in order to improve the location of each signal induced by the application of a corresponding stimulus signal and to improve said distinction between the electric signals induced by the stimuli and the signals indicative of brain activity, be it natural activity or the result of the applied stimuli, upon analyzing the monitored signals.

For one embodiment, said marking signal corresponds to the direct sequence spread spectrum, or DSSS, of a pure sinusoidal signal which generates a signal with a power density below the noise level of the monitored signal, for example EEG.

The process for recovering the signal dispersion in each tomography voxel allows recovering the contribution made by each stimulation element in each voxel (using the superposition principle) and it is used, applying the method proposed by the first aspect of the invention, to improve the guiding by means of adjusting the intensities of the stimulus signals applied in the different stimulation elements.

For another embodiment, the method comprises using the process for recovering the dispersion prior to performing the tomography since the process is a linear process.

For one embodiment, the marking signal is the same in each stimulus-supplying stimulation element but its spectrum is spread using pseudo random noise, or PRN, codes, as is common in code division multiple access, or CDMA, systems such as those used in GPS systems, in mobile telephones in the United States, etc.

The sensors used to acquire the monitoring signals thus receive all the contributions caused by the stimulus signals with a power below that of the signal representative of the brain activity present in the monitored signal, for example by means of EEG.

By means of the application of the method proposed by the first aspect of the invention, the complex activation patterns of the brain are reproduced in a controlled manner through a model.

The multi-site cranial stimulation performed according to the proposed method also allows:
  Freedom for adjusting to the specific rhythms and patterns in the oscillating brain;
  Improving the focus on specific sites;
  A stimulation coordinated in space and time throughout the entire cortex;
  A control of frequency and phase relationships in each site;
  A self-calibration or adaptation of the stimulation as a result of the real-time feedback of the monitored signals.

In a second aspect, the present invention also relates to a multi-site cranial stimulation system which comprises:

a plurality of stimulation elements arranged adjacent to a corresponding plurality of different regions of a brain, and an electronic system in connection with said plurality of stimulation elements and provided for applying thereto corresponding stimulus signals for the purpose of individually stimulating said plurality of regions of said brain, but not to achieve a local result in each region as a result of each individual stimulus, but rather to obtain an overall result caused by the synergy of said individual stimuli.

In order to obtain said overall result in a characteristic manner the mentioned electronic system of the proposed stimulation system comprises one or more processing units with access to one or more simplified models of the brain or of one or more sectors thereof, considered the brain or said sector thereof as a non-linear coupled oscillating system, said processing unit or units being provided for determining said stimulus signals so that they are suitable for exciting at least one natural vibration mode of said non-linear coupled oscillating system.

The system proposed by the second aspect of the invention comprises a series of electrophysiological sensors arranged adjacent to specific regions of the brain and in connection with said processing unit of said electronic system for monitoring the brain activity of said brain.

For one embodiment, said electrophysiological sensors are arranged coinciding in space with the stimulation elements, for a variant of said embodiment, each stimulation element and each electrophysiological sensor being one and the same element capable of performing both stimulating and monitoring functions.

The placement system used can be any known standard system such as the 10/30 system of electrode placement. As for the mentioned processing unit, it is provided for controlling said stimulus signals depending on said monitored brain activity.

The system proposed by the second aspect of the invention is provided for carrying out the mentioned multi-site cranial stimulation by means of the application of the method proposed by the first aspect of the invention for which the mentioned processing unit implements a series of algorithms by means of which the different steps of the method are carried out, specifically steps related to the access and analysis of the simplified model or models of the brain (and for one embodiment, it also relates to the construction of said models), to the determination of the stimulus signals based on said model or models, to the analysis of the monitored signals and their use for adapting the stimulus signals in real-time during the operating period of the cranial stimulation, as well as in an initial phase which includes the different guiding and calibrating steps described above.

For one embodiment, the method comprises carrying out said determination of said stimulus signals from the calculation of currents generated in a bipolar manner between two of said stimulation elements upon applying specific stimulus signals to them, and using superpositioning techniques for the calculation of generated multi-site currents, said techniques assuming that the stimulation effect applied by means of the entire set of stimulation elements will be the superposition of the stimulation effect applied in each pair of stimulation elements.

For one embodiment, the method proposed by the first aspect of the invention comprises determining said stimulus signals to reduce or suppress a specific brain activity.

The applications of the proposed method and system are very wide-ranging, including those related to:

Research: Cognitive psychology/neuroscience by means of which the causality can be determined. It has been demonstrated that the plasticity of the human brain can also be measured with repetitive TMS stimulation (and the variants of this technique such as theta-burst stimulation or paired associative stimulation).

Diagnosis: TMS stimulation is currently used on a clinical level to measure the activity and the function of specific brain circuits in human beings.

Therapy: TMS stimulation is currently used to treat several neurological conditions such as migraines, strokes, epilepsy, Parkinson's disease, dystonia or tinnitus, as well as psychiatric conditions such as clinical depression or auditory hallucinations.

Brain-machine interface: Communication from machines to the brain, and vice versa.

Sensory synthesis: Creation of new senses by means of coupling data sources directly to the human brain Although there are earlier works on some of said applications as indicated, the application of the method and the system proposed by the present invention seek to greatly improve the results obtained, as well as the functionality and freedom for adjustment and adaptation of the different parameters inherent to the stimulation systems compared to conventional proposals.

BRIEF DESCRIPTION OF THE DRAWINGS

The foregoing and other advantages and features will be more fully understood from the following detailed description of an embodiment in reference to the attached drawings which must be interpreted in an illustrative and non-limiting manner, in which:

FIG. 1 is a schematic depiction of the system proposed by the second aspect of the present invention for one embodiment.

DETAILED DESCRIPTION OF AN EMBODIMENT

FIG. 1 illustrates the system proposed by the second aspect of the invention for an embodiment in which a patient H is provided with the aforementioned plurality of stimulation elements E1, E2 . . . En (schematically depicted by a small circle which represents an ordered assembly or array of electrodes) adjacent to a corresponding plurality of different regions of the brain.

As described above, the system proposed by the second aspect of the invention also comprises a series of electrophysiological sensors S1, S2 . . . Sn arranged adjacent to specific regions of the brain and in connection with said processing unit of said electronic system to monitor the brain activity of said brain. Said electrophysiological sensors S1, S2 . . . Sn are also illustrated in FIG. 1 adjacent to the brain of patient H (they are also schematically depicted by a small circle which represents an ordered assembly or array of sensors).

The proposed system comprises an electronic system in connection with said plurality of stimulation elements E1, E2 . . . En provided for applying thereto corresponding stimulus signals for the purpose of individually stimulating said plurality of regions of said brain, although as mentioned in one of the preceding sections, the real purpose of the system proposed by the second aspect of the invention is not the individual result obtained in each stimulated region (as in the case of the conventional proposals), but the synergy that is produced upon stimulating each region with specific stimulus signals, resulting in the excitation of a natural vibration mode of the brain, or of a sector thereof, this being understood as a non-linear coupled oscillating system.

Said electronic system comprises a local SCM system which, for one embodiment, is supported by a support (not illustrated) which also supports said stimulation elements E1, E2 ... En and said electrophysiological sensors S1, S2 ... Sn. Although said support has not been illustrated in FIG. 1, for one embodiment it is illustrated in FIGS. 4a to 4e of Spanish utility model with publication number 1067908, belonging to the present applicant, and indicated with reference C which, as can be seen in said FIGS. 4a to 4e of said utility model, and in the corresponding description thereof, is configured to be attached on the head of a patient H, positioning the stimulation elements, in this case E1, E2 ... En, and sensors, in this case those indicated as S1, S2 ... Sn, in the mentioned regions adjacent to said specific regions of the brain.

For one embodiment, the proposed system comprises display means, such as a display, provided to show in time-real or almost real-time a map of the programmed stimulation from the specific stimulus signals and a map of the monitored brain activity, preferably simultaneously.

Preferably, although the system is not limited to it, the stimulation carried out by means of the system proposed by the second aspect of the invention is of the transcranial type, using noninvasive stimulation elements.

As illustrated in FIG. 1, the local electronic system SCM is suitable for communicating wirelessly with a remote electronic system SR comprised by said electronic system, for which purpose it comprises a communications module suitable for such purpose (not illustrated) which is indicated as working with the IEEE802.15.4 specifications in FIG. 1, however, for other embodiments it can operate with another wireless communications technology and/or protocol.

The local electronic system SCM is suitable for performing the functions described for the local system which is also referred to as SCM in said utility model ES1067908U, for conditioning biopotential signals (in the manner described in said utility model or in another manner), but it is further adapted to carry out, in part or in its entirety, the previously described steps for determining and adapting the stimulus signals as well as the conditioning thereof (D/A conversion, etc.) and supplying stimulus to the stimulation elements E1, E2, ... En, receiving and analyzing the monitored signals through the sensors S1, S2 ... Sn, accessing the simplified model or models, guiding, calibrating, etc.

Said local electronic system SCM comprises a battery, not illustrated, and, depending on the final requirements, it is suitable for providing signals with different frequencies, phases and amplitudes among different stimulation elements.

In short, the local electronic system SCM controls the stimulation elements/monitoring sensors, and it is communicated wirelessly with a remote electronic system SR, forming a wireless, portable and completely digital system.

For one embodiment, the local electronic system SCM includes a memory to store the data on-board, allowing the SCM to function autonomously.

For one embodiment, said remote system SR implements a stimulation/monitoring application which, for the variant illustrated by FIG. 1, is bidirectionally accessible through the TCP/IP protocol and is connected to a processing unit PDPU through a USB controller.

Said processing unit PDPU for the illustrated embodiment is a personal data processing unit PDPU that incorporates a communications module (not illustrated) suitable for wireless bidirectional communication with the corresponding communications module of the local electronic system SCM, acting as an interface between the system SCM and the remote system SR.

For one embodiment, the wireless communication between the local system SCM and the processing unit PDPU is based on Low-Rate Wireless Personal Area Networks (LR-WPANs) and, as indicated above, the monitoring is based on the circuit described in utility model ES1067908U.

The DSSS processing described above, as well as the synchronization of the marking signals, the control of the stimulation elements which apply the stimulus signals, the sampling, the process for recovering the dispersion of the marking signals, as well as the phase-lock loop PLL algorithms used for tracking the phase of the marking signals, require intensive digital signal processing which is carried out in real-time in the local system SCM. To that end, the digital processing is carried out for one embodiment by means of an in-situ field programmable gate array, or FPGA, with an integrated processor in order to maintain the power requirements to a minimum.

A person skilled in the art will be able to introduce changes and modifications in the described embodiments without departing from the scope of the invention as it is defined in the attached claims.

The invention claimed is:

1. A multi-site cranial stimulation method, comprising applying individual stimuli to different regions of a brain by means of the application of specific stimulus signals to corresponding stimulation elements arranged adjacent to said regions of said brain, wherein said cranial stimulation is a transcranial alternating current electrical stimulation wherein said stimulation elements used are noninvasive, wherein the method comprises constructing at least one simplified model of the brain or of a sector thereof, considering the brain or said sector thereof as a non-linear coupled oscillating system, and comprises determining said stimulus signals so that they are suitable for exciting at least one natural vibration mode of said non-linear coupled oscillating system, and wherein the method further comprises adapting or self-calibrating in real time said stimulus signals to the changes observed in the brain activity, by means of:
monitoring the brain activity of said brain at least prior to and/or during the application of said stimulus signals,
using one or more analysis techniques applied to said monitored signals to distinguish between the electric signals induced by the stimuli and natural bioelectric signals or response signals to said stimuli,
considering said electric signals induced by the stimuli as unwanted signals, and performing a proper filtering of the monitored signals in order to clean said unwanted signals from those which are really indicative of brain activity; and
controlling said stimulation by means of varying said stimulus signals depending on the monitored brain activity, from the filtered monitored signals free of said unwanted signals.

2. The method according to claim 1, wherein the method comprises performing said application of said stimulus signals in a manner coordinated in space, regarding the electric field distribution on the cortex, and time.

3. The method according to claim 2, wherein the method comprises simultaneously applying at least part of said stimulus signals to produce the excitation of at least one natural vibration mode of the brain or of said section thereof by means of the application of said stimulus signals.

4. The method according to claim 2, wherein said regions to be stimulated extend substantially throughout the cerebral cortex of said brain.

5. The method according to claim 1, wherein the method comprises independently controlling the phase, frequency and amplitude of each of said stimulus signals to consequently vary the phase, frequency, and amplitude of the induced electric signals.

6. The method according claim 1, wherein the method comprises constructing a plurality of said simplified models for a corresponding plurality of sections of the brain, and in that it comprises determining and controlling said stimulus signals so that they are suitable for selectively exciting one or more natural vibration modes of one or more of the non-linear coupled oscillating systems corresponding to said simplified models of said sections of the brain.

7. The method according claim 1, wherein the method comprises focusing the individual stimuli by means of a first step, or a guiding step, in which the stimulus signals to be applied to the stimulation elements are determined and controlled depending on the brain region with respect to which they are arranged adjacently, and the mentioned focusing is improved by means of a second step, or calibrating or adjusting step, in which said variation of the stimulus signals is carried out according to the monitored signals.

8. The method according to claim 1, wherein said analysis techniques are at least a technique from the group comprising the following techniques: frequency separation technique, time separation technique and tomography technique, or a combination thereof.

9. The method according to claim 1, wherein the method comprises using spread spectrum techniques applied to said monitored signals to identify the activity associated with the stimulation in each stimulation element.

10. The method according to claim 1, wherein the method comprises associating a marking signal to each of the stimulus signals to improve the location of each signal induced by the application thereof, and to improve said distinction between the electric signals induced by the stimuli and the response signals to said stimuli upon analyzing the monitored signals.

11. The method according to claim 1, wherein the method comprises carrying out said determination of said stimulus signals from the calculation of the currents generated in a bipolar manner between two of said stimulation elements upon applying specific stimulus signals to them, and using superpositioning techniques for the calculation of generated multi-site currents.

12. The method according to claim 1, wherein the method comprises determining said stimulus signals to suppress a specific brain activity.

13. A multi-site cranial stimulation system which comprises:
a plurality of stimulation elements (E1, E2 ... En) arranged adjacent to a corresponding plurality of different regions of a brain,
an electronic system in connection with said plurality of stimulation elements (E1, E2 ... En) and provided for applying thereto corresponding stimulus signals for the purpose of individually stimulating said plurality of regions of said brain,
wherein said electronic system comprises at least one processing unit with access to at least one simplified model of the brain or of a sector thereof, being considered to be a non-linear coupled oscillating system, and provided for determining said stimulus signals so that they are suitable for exciting at least one natural vibration mode of said non-linear coupled oscillating system,
wherein said cranial stimulation is a transcranial alternating current electrical stimulation wherein said stimulation elements used (E1, E2 ... En) are noninvasive,
wherein the system comprises a series of electrophysiological sensors (S1, S2 ... Sn) arranged adjacent to specific regions of the brain and in connection with said processing unit of said electronic system, and intended for monitoring the brain activity of said brain at least prior to and/or during the application of said stimulus signals,
wherein said processing unit is provided for adapting or self-calibrating in real time said stimulus signals to the changes observed in the brain activity, by means of:
implementing one or more analysis techniques applied to said monitored signals to distinguish between the electric signals induced by the stimuli and natural bioelectric signals or response signals to said stimuli, and
under the consideration that said electric signals induced by the stimuli are unwanted signals, implementing a proper filtering of the monitored signals in order to clean said unwanted signals from those which are really indicative of brain activity, and varying said stimulus signals depending on the monitored brain activity, from the filtered monitored signals free of said unwanted signals.

14. The system according to claim 13, wherein said electronic system comprises at least one local system (SCM) supported by a support which also supports said stimulation elements (E1, E2 ... En) and said electrophysiological sensors (S1, S2 ... Sn), said support being configured to be attached on the head of a patient (H), positioning the stimulation elements (E1, E2 ... En) and sensors (S1, S2 ... Sn) in the mentioned regions adjacent to said specific regions of the brain.

15. The system according to claim 14, wherein said local electronic system (SCM) comprises on-board data storage.

16. The system according to claim 14, wherein said local electronic system (SCM) comprises a communications module suitable for communicating wirelessly with a remote electronic system (SR) comprised by said electronic system.

* * * * *

UNITED STATES PATENT AND TRADEMARK OFFICE
CERTIFICATE OF CORRECTION

PATENT NO.        : 8,660,649 B2
APPLICATION NO. : 13/058886
DATED             : February 25, 2014
INVENTOR(S)       : Ruffini et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this

Twenty-ninth Day of September, 2015

Michelle K. Lee
*Director of the United States Patent and Trademark Office*